United States Patent [19]

Elzinga et al.

[11] 4,101,774
[45] Jul. 18, 1978

[54] X-RAY SYSTEM HAVING A DRIVING MECHANISM FOR AN X-RAY SOURCE AND AN X-RAY DETECTOR

[75] Inventors: Johannes Mattheus Elzinga; Albertus Derk Sondern, both of Eindhoven, Netherlands

[73] Assignee: U.S. Philips Corporation, New York, N.Y.

[21] Appl. No.: 765,525

[22] Filed: Feb. 4, 1977

[30] Foreign Application Priority Data

Feb. 6, 1976 [NL] Netherlands ............................ 7601219

[51] Int. Cl.² ........................................... H05G 1/00
[52] U.S. Cl. ............................... 250/402; 250/445 T
[58] Field of Search .................... 250/445 T, 401, 402

[56] References Cited

U.S. PATENT DOCUMENTS 3,714,427  1/1973  Reiniger ........................ 250/445 T
3,809,886  5/1974  Cochran ........................ 250/445 T Primary Examiner—Craig E. Church
Attorney, Agent, or Firm—Frank R. Trifari; Jack E. Haken

[57] ABSTRACT

The tomography movements of the X-ray source and detector are matched electronically to each other by comparing the positions thereof. Via a memory, a weighed position for the source is determined with reference to a desired velocity ratio and the position of the X-ray source, which position is compared to the actual position of the detector. The difference between the two determines the value of a correction signal for controlling the driving means of the X-ray detector.

9 Claims, 4 Drawing Figures

X-RAY SYSTEM HAVING A DRIVING MECHANISM FOR AN X-RAY SOURCE AND AN X-RAY DETECTOR

The invention relates to an X-ray system for making a shadow image of a layer of an object, which X-ray system comprises an X-ray source and an X-ray detector, as well as driving means which are designed to move the X-ray source and the X-ray detector with respect to each other in at least substantially parallel planes and with a constant velocity ratio, in which the driving means comprise the following components:

at least one electric motor driving the X-ray source, at least one electric motor driving the X-ray detector, each electric motor being connected to an electronic control circuit to control the number of revolutions of said motor, an electric coupling existing between the electric motors. Such an X-ray system is disclosed in U.S. Pat. No. 3,809,886. The system described in that specification comprises an electric coupling between the X-ray source and the X-ray detector so as to keep the two in the correct position relative to each other. The said coupling is a coupling between synchronous motors, in which a possible position error between the X-ray source and detector is not removed by the said coupling.

It is the object of the invention to avoid the above drawback and to provide an X-ray system which enables a more accurate adjustment of the mutual positions of X-ray source and detector.

For that purpose, an X-ray system according to the invention is characterized in that the electric coupling comprises signal generators which are connected to the electric motor and/or to the X-ray source and X-ray detector driven by electric motors so as to obtain signals which are a measure of the instantaneous position of the X-ray source and detector, at least one comparison circuit which is connected to the signal generators for deriving from the signals generated by the signal generators a correction signal for a control circuit of one of the said electric motors, all this in such manner that the movements of the X-ray source and detector are matched to each other, a controllable inverter circuit being arranged between the comparison circuit and the control circuit and being either in a first operating condition or in a second operating condition, as the need may be, the correction signal from the comparison circuit being inverted in the first operating condition and being not inverted in the second operating condition. The instantaneous positions of the X-ray source and detector are compared with each other. By means of the electric coupling according to the invention, a position error and, with reference thereto, a correction signal is determined, so that an accurate position relationship is realized between the X-ray source and detector.

An embodiment of an X-ray system according to the invention is characterized in that the comparison circuit is designed to convert a first signal generated by one of the signal generators into a comparison signal with reference to an adjustable weighing code, the correction signal being equal to the difference between the comparison signal and a second signal generated by the second signal generator, all this in such manner that the weighing code determines the velocity ratio of the X-ray source and detector. The possibility of electronically adjusting the velocity ratio of the X-ray source and detector is very useful since herewith a shadow image can be made of an object of layers differing in height, it being superfluous to displace the object or the X-ray source and detector in height. The adjustability in height of a table on which the object is situated becomes superfluous, which results in considerable savings as regards the construction of the table.

In order to obtain an optimum shadow image — a sharp and contrasting reproduction of the desired layer — the angle traversed by the X-ray source and detector with respect to a point of rotation in the layer to be reproduced, and the exposure time should preferably be matched to each other completely. Therefore, the X-ray system according to a preferred embodiment of the invention is characterized in that a velocity selection circuit is present for controlling the control circuits of the electric motors, which circuit is designed to form from a section-height signal and a movement-width signal a velocity signal which serves as an input signal for the control circuits of the electric motors, the section-height signal indicating the point of rotation of the connection line between the X-ray source and detector and the movement-width signal indicating an angle to be traversed by the connection line relative to the point of rotation and a period of time for traversing the angle.

An embodiment of the X-ray system according to the invention is characterized in that the comparison circuit comprises the following components:

counters for counting pulses generated by the signal generators, of which counters a counter position can be read periodically, a first buffer for storing the counter position of a first counter, a selection circuit with which in a first operating condition the counter position of a second counter can be presented directly to a second buffer and, in a second operating condition, the said counter position can be presented to a weighing code memory, the weighing code memory in which the weighing code is stored for converting the counter position of the second counter into the comparison signal, the second buffer for storing either the counter position, or the counter position of the second counter converted with the weighing code memory a subtraction circuit for determining a difference in contents of the first and second buffer, a third buffer for storing the difference-in-contents can be stored, which difference-in-contents determines the value of the correction signal. The use of counters and buffers involves the advantage of monitoring the position of the X-ray detector with respect to the position of the X-ray source. Not the velocity of the X-ray source and X-ray detector is compared, but the integral thereof, which leads to a position error equal to zero. Due to the desired movement accuracy of the X-ray source and detector with respect to each other, the position comparison described constitutes a preferred embodiment.

An embodiment according to the invention of an X-ray system in which the X-ray source and detector make two-dimensional movements which are matched to each other is characterized in that the X-ray source and detector are each driven by two motors for moving the X-ray source and detector in two substantially parallel planes in two directions normal to each other, the X-ray source and detector having a constant velocity ratio, the X-ray system comprising at least two weighing code memories and at least two velocity selection circuits and a movement in a first direction can be determined by means of a combination of a first weighing code memory and a first velocity selection circuit, and a movement which is normal to the first direction can be determined by means of the combination of the second weighing code memory and the second velocity selection circuit by presenting a section-height signal to the two memories and to the two velocity selection circuits; a movement-width signal being dependent on time and consisting of two components the first component of which is presented to the memory and to the velocity selection circuit of the first combination and the second component is presented to the memory and to the velocity selection circuit of the second combination. The realization of two-dimensional movements is not restricted by a mechanical construction so that theoretically the number of movement patterns to be performed is unlimited.

The invention will be described in greater detail with reference to a drawing, in which.

Figure 1:
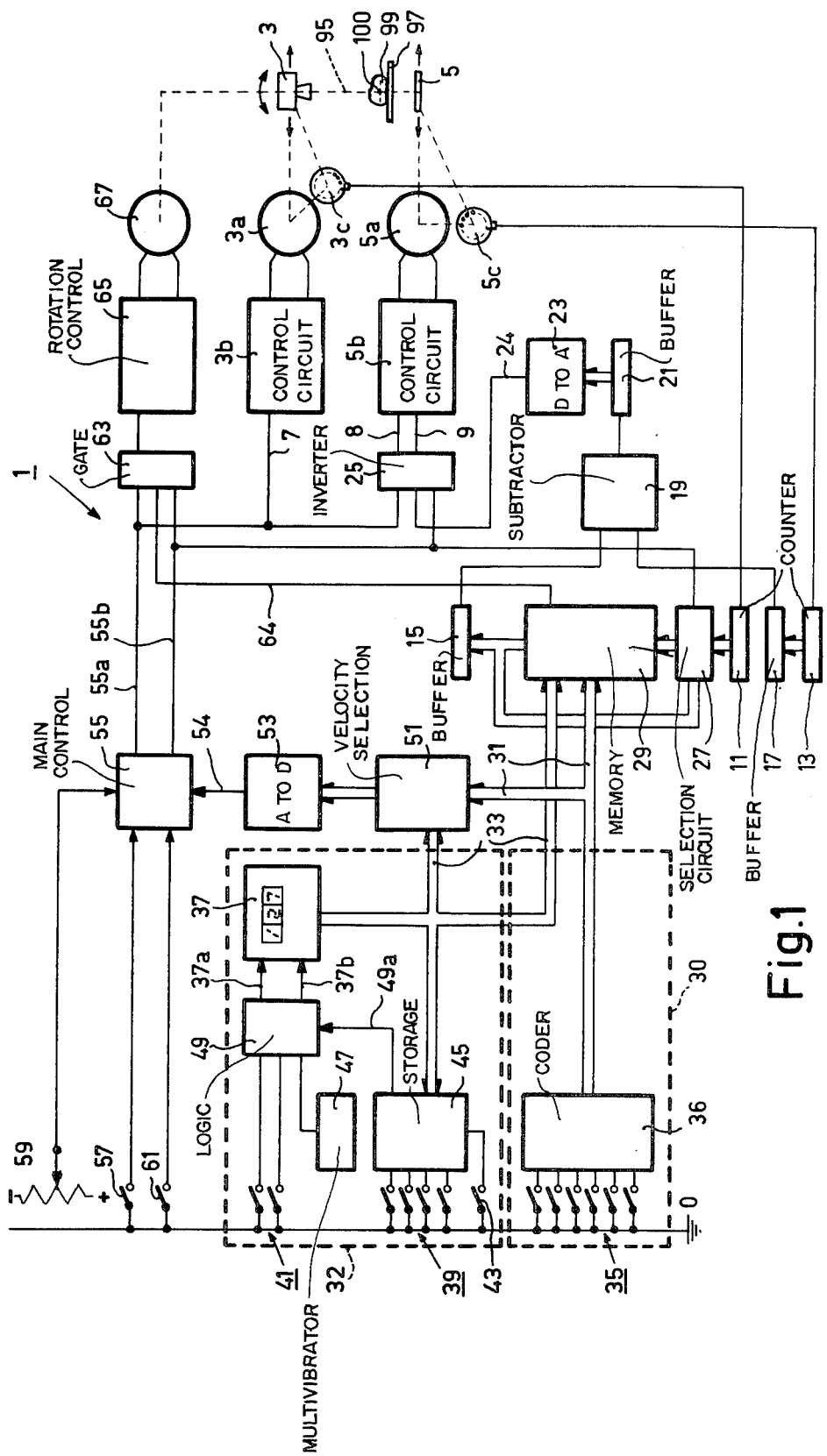
FIG. 1 shows a basic diagram for matching the movement of the X-ray source and detector according to the invention.

The movements of the X-ray source 3 and the detector 5 can be matched to each other by means of the basic diagram 1 shown in FIG. 1.

The X-ray source 3 and detector 5 are moved in the same direction or in opposite directions with respect to an object 99 which is positioned on a table 97. In the latter case, a connection line 95 between the source 3 a point 100 in the object 99 will rotate about a point 100. In the ideal case, the connection line 95 is also a connection line between the X-ray source 3 and the detector 5. The X-ray source 3 and detector 5 are driven by direct current motors 3a and 5a, respectively. The motors 3a, 5a are controlled by control circuits 3b, 5b. The control circuit 3b receives a control signal via input 7 and the control circuit 5b receives the same control signal via input 8 and a correction signal via input 9 which in value corresponds to the deviation in position of the X-ray detector 5 with respect to the connection line 95. The correction signal is determined as follows. Disks 3c and 5c are connected to the X-ray source 3 and detector 5, respectively, the speed of rotation of which is proportional to the speed of the source 3 and detector 5, respectively. Holes are provided upon the periphery of the disks 3c, 5c. In cooperation with a light source and photodiode (not shown in the drawing) the rotating disks 3c, 5c generate pulse series which are a measure of the displacement of the source 3, detector 5 respectively. The generated pulses are counted by counters 11 and 13. The counter position of counter 11 indicates the position of the source 3 and the counter position of counter 13 indicates the position of detector 5. The contents of counters 11 and 13 are read periodically and stored in the buffers 15 and 17, respectively. The difference between the contents of buffers 15 and 17 is determined by a subtraction circuit 19 and is stored in a buffer 21. By means of a digital-to-analog converter 23, the difference in analog form which is inverted or is not inverted by the controllable inverter circuit 25, is presented as a correction signal to the control unit 5b via input 9.

When the control signal and the correction signal are inverted by means of the inverter circuit 25, the source 3 and detector 5 both move in the same direction with respect to an object 99 situated between the source 3 and the detector 5, after which as a result of the displacement a record can be made of another part or of another object. The velocities of the source 3 and detector 5 are the same during the said movement. This is achieved by equalising the number of pulses to be counted by the counters 11 and 13 and introducing the contents of counter 11 directly into the buffer 15 by means of a selection circuit 27.

When the control signal and the correction signal are not inverted, the source 3 and detector 5 have opposite directions of movement. The contents of counter 11 in that case are introduced into a weighing code memory 29 via the selection circuit 27. The signal from the weighing code memory 29 is stored in buffer 15 and is a conversion of the contents of counter 11. The conversion takes place with reference to a weighing code which is selected from a matrix and is fixed in the weighing code memory 29. The selection of the weighing code occurs with the movement-width signal via entry 31 and with the section-height signal via entry 33 which are generated by the units 30 and 32, respectively. The said signals together determine the velocity at which the source 3 will move and the velocity ratio between the source 3 and detector 5. The velocity ratio determines the distance between point 100 and the detector 5, and so which layer from an object 99 to be X-rayed will be reproduced sharply. Making the velocity ratio adjustable electronically presents the possibility of reproducing several layers of an object, it being superfluous to vary mutual positions of the object 99, the source 3 or the detector 5 in height.

Unit 30 comprises a few switches 35 and a coder circuit 36. Each switch 35 presents the possibility of making a photograph with a different exposure time or a different angle to be traversed during the exposure through the connection line 95 of the source 3 and detector 5. The coder circuit 36 comprises, for example, a diode matrix circuit with which the choice is presented to the weighing code memory 29 and a velocity selection circuit 51 as a binary signal in bit-parallel form. The velocity selection circuit 51 is controlled by signals via entries 31 and 33 and has the following task. By means of the signals on the entries 31 and 33, a velocity signal is selected in the velocity selection circuit 51 from a collection of velocity signals which are stored in a matrix in the velocity selection circuit 51. The velocity circuit is preferably a read-only memory. Via an analog-to-digital convertor 53, the velocity signal is presented to a main control circuit 55 via connection 54. The main control circuit 55 can put the velocity signal on connection 55a and present it to the control circuit 3b and 5b as a control signal via inputs 7 and 8. The function of the main control circuit 55 will be explained hereinafter.

The signal on entry 33 establishes the point of rotation of the connection line between the source 3 and the detector 5. By means of unit 32, the signal is obtained as follows. Circuit 37 comprises a counter, a binary-to-decimal converter and a digit display device, with which the adjusted distance between the point of rotation 100 and the line along which the detector moves is displayed in mm. The value of the variation of the distance is adjusted by means of switches 39. It can be indicated by means of switches 41 whether the distance has to be increased or decreased. After actuating switch 43, the contents of counter 37 are stored in a storage and comparison circuit 45 in which the contents of the counter 37 and the value of the variation of the distance are added. A multivibrator 47 feeds, via a logic circuit 49, pulses to counter 37 to which the pulses are presented to addition or substraction inputs 37a and 37b, respectively, in accordance with the position of switches 41. The new position of the counter 37 is compared continuously with the old position of memory and comparison circuit 45 and the variation added thereto. As soon as said new position corresponds to the desired position, the pulses of multivibrator 47 are blocked in the logic circuit 49 by means of a stop signal via connection 49a. The new position is maintained in the counter 37 and is presented via entry 33 to the velocity selection circuit 51 and the weighing code memory 29.

The main control circuit 55 is switched to a first or in a second operating condition by means of a switch 57. In the second operating condition of the main control circuit 55, input 54 can be connected to the connection 55a and inputs 7 and 8 of control circuits 3b and 5b by means of switch 61. The source 3 and detector 5 are moved in opposite directions. In the first operating condition, the inverter circuit 25 and the selection circuit 27 are actuated via connection 55b. The source 3 and detector 5 are controlled in the same direction, the value of the velocity and the direction being determined by the voltage which is tapped from potentiometer 59. The said voltage is applied to connection 55a and serves as a control voltage for the control circuit 3b and 5b.

The connections 55a and 55b are also coupled to a gate circuit 63. In the second operating condition of the main control circuit 55 the control signal is also transmitted to the rotation control circuit 65 which controls an electric motor 67. The source 3 and detector 5 are moved in opposite directions, the motor 67 rotating the source 3 in such manner that the source 3 remains directed onto the point of rotation 100. The rotation control circuit 65 is activated only after it has been established, via the weighing code memory 29, that the position of the source 3 corresponds to the initial position associated with the selected tomographic movement. In the first operating condition of main control circuit 55, the control signal presented to connection 55a is cut off in the gate circuit 63 by activating the gate circuit 63 via connection 55b.

Figure 2:
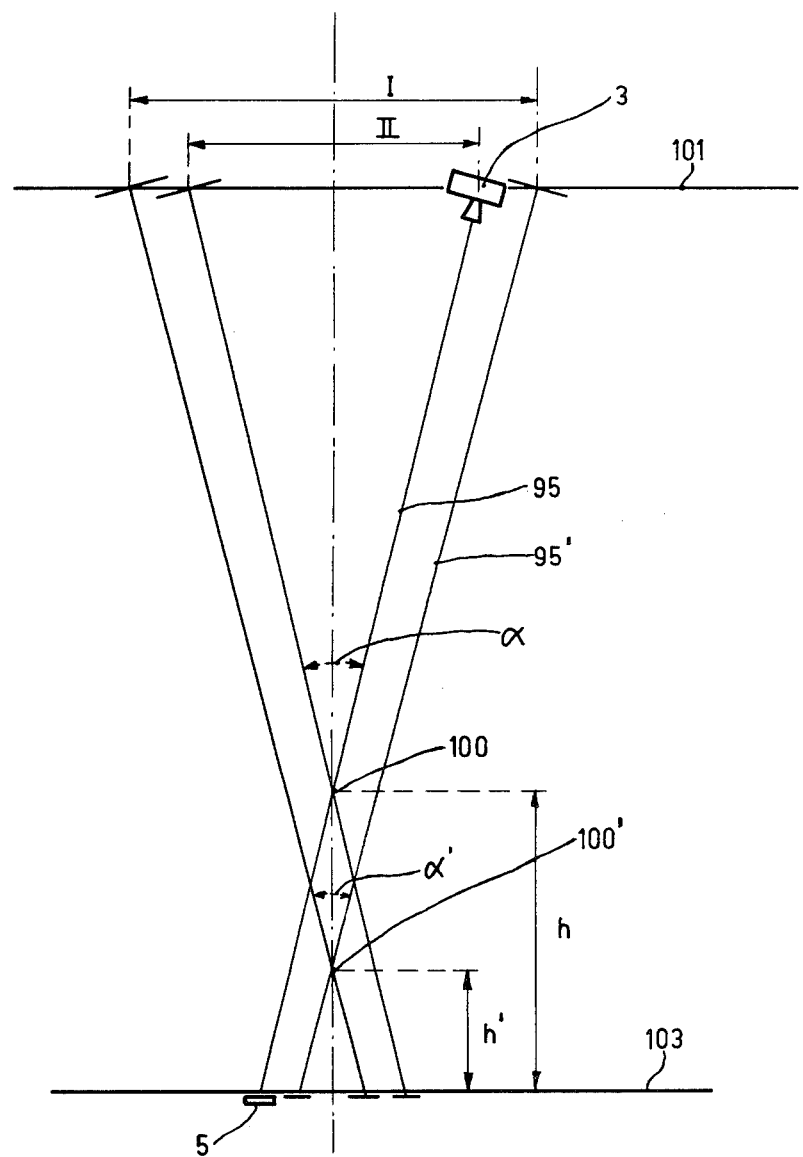
FIG. 2 shows diagrammatically the effect of the variation of the velocity ratio of the X-ray source and detector.

FIG. 2 shows two lines 101 and 103 along which the X-ray source 3 and the X-ray detector 5, respectively, move. Also shown is a maximum and a minimum distance h and h', respectively, of points of rotation 100 and 100', respectively, to the line 103 along which the detector 5 moves. The angles α, α' to be traversed by the connection line 95 are equally large in both points of rotation 100, 100'. The distances I, II to be covered by the source 3 are not equal. When the same exposure time is used, the speed of the source 3 will have to be adapted. This also applies to the velocity ratio of the source 3 and the detector 5, as will be obvious from FIG. 2.

Figure 3:
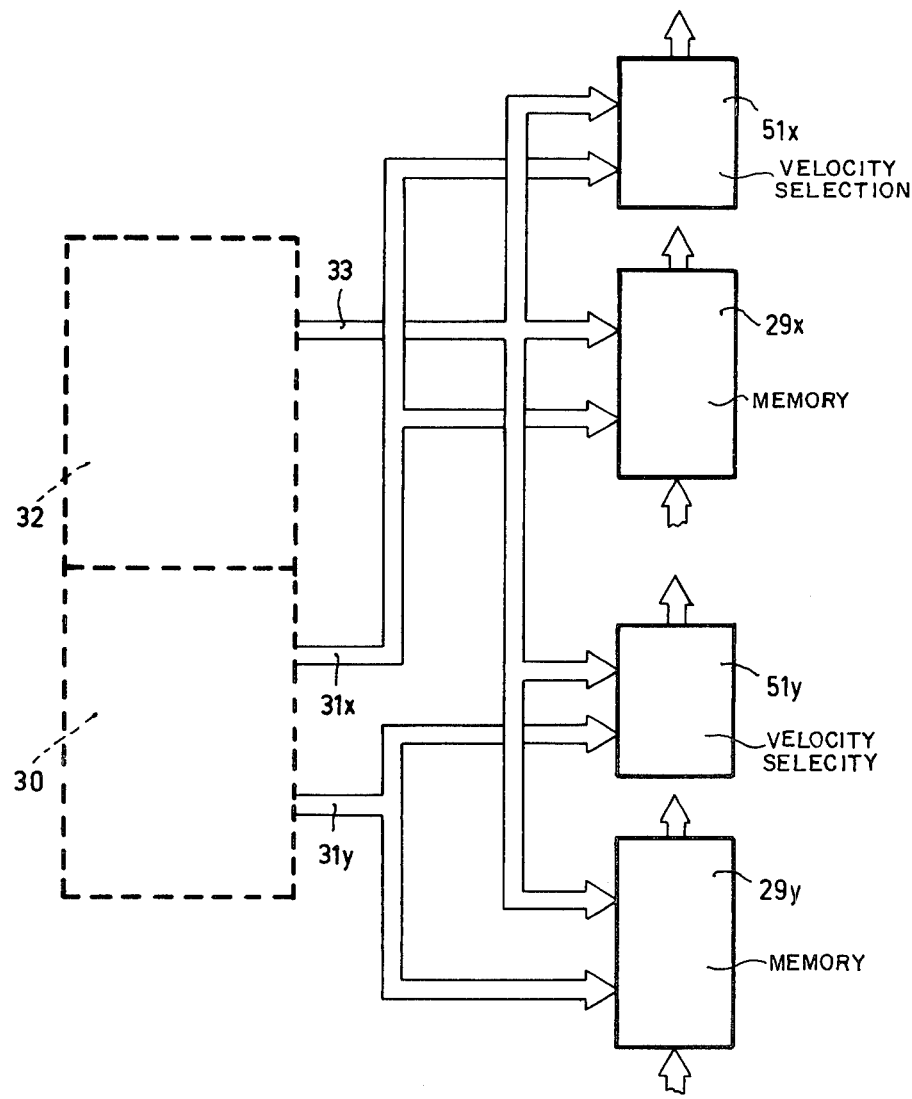
FIG. 3 is a block diagram of a control to obtain a two-dimensional matched movement of the X-ray source and detector according to the invention.

The basic diagram 1 shown in FIG. 1 may be applied to X-ray systems in which the source 3 and the detector 5 perform a univariate movement. FIG. 3 shows a principle to match two dimensional movements of an X-ray source and detector 5 to each other. It is useful to resolve two dimensional movements into two univariate movements perpendicular to each other. For that purpose, the circuit of FIG. 3 has two velocity selection circuits 51x and 51y and two weighing code memories 29x and 29y. The distance from the point of rotation 100 to the source 3 and detector 5 is adjusted by means of a unit 32. Via entry 33 a signal generated by unit 32 is presented to both memories 29x, 29y and to both selection circuits 51x and 51y. The selected movement pattern is fixed by means of unit 30. The unit 30 provides on each entries 31x and 31y a signal, each of which is variable as a function of time. The velocity selection circuits 51x and 51y, respectively, determine, from the signals presented via the entries 31x and 33 and 31y and 33, respectively, the instantaneous velocities of the source 3 in the x and y-directions, respectively. The weighing code memories 29x and 29y, respectively, determine, from the signals presented via the entries 31x and 33 and 31y and 33, respectively, the instantaneous weighing code with which the x and y-positions, respectively, of the source 3 have to be converted so as to match the velocity ratio of source 3 and detector 5 to each other in the x- and y-directions, respectively. In order to avoid disturbances in the relations between the velocities in the x and y-directions as a result of, for example, frictional and accelerating forces, it is useful to match the velocity in one direction via an electronic control system to the velocity in the other direction.

Figure 4:
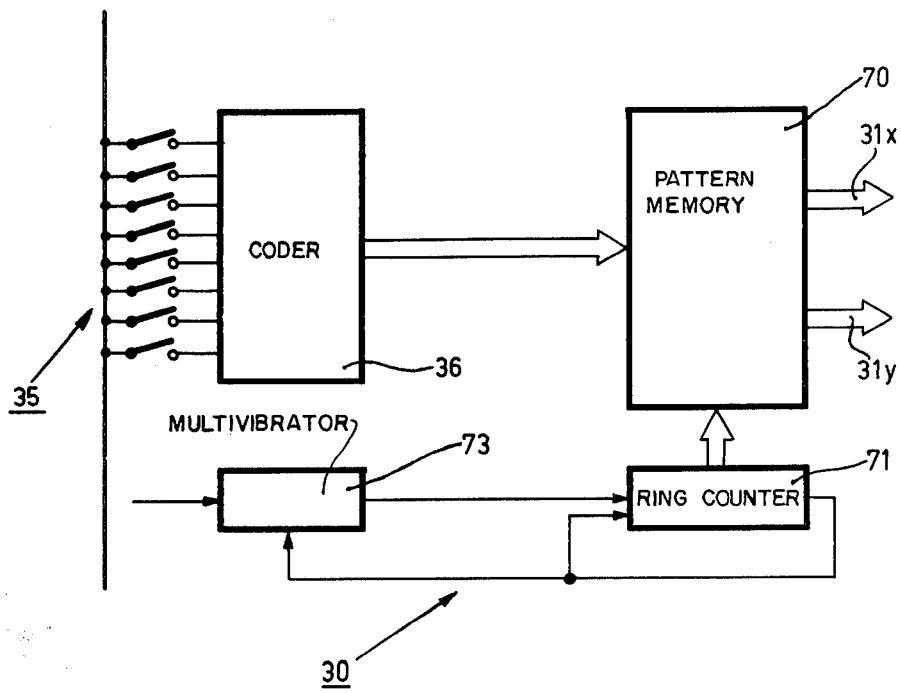
FIG. 4 is a principle diagram of a part of the control shown in FIG. 3.

FIG. 4 shows the unit 30 of FIG. 3 in greater detail. By means of one of the switches 35, a movement pattern is selected from a collection of movement patterns. The choice is presented to the pattern memory 70 in a digital form by a coding device 36. The successive movement signals which determine the movement of the X-ray source 3 and detector 5 in the x and y-directions, are stored in the pattern memory 70. The successive movement signals are read step by step and are presented at entries 31x and 31y by control of a ring counter 71. The ring counter 71 is activated by pulses of a multivibrator 73. The multivibrator 73 is started by a signal at input 75 which is generated by the main control circuit 55 (not shown) when this is switched to the second operating condition. The multivibrator 73 is stopped by ring counter 71, when the ring counter 71 has traversed all positions.

What is claimed is:

1. An X-ray system for making a shadow image of a layer of an object, which X-ray system comprises an X-ray source and an X-ray detector, as well as driving means which are designed to move the X-ray source and the X-ray detector with respect to each other in at least substantially parallel planes and with a constant velocity ratio in which the driving means comprise, in combination:
at least one electric motor driving the X-ray source;
at least one electric motor driving the X-ray detector, each electric motor being connected to an electronic control circuit to control the number of revolutions of said motor, an electric coupling existing between the electric motors; wherein the electric coupling comprises:
signal generators which are connected to the electric motor and/or to the X-ray radiator and detector driven by electric motors so as to obtain signals which are a measure of the instantaneous position of the X-ray source and detector;

at least one comparison circuit which is connected to the signal generators and functions to derive from the signals generated by the signal generators a correction signal for a control circuit of one of the said electric motors, whereby the movements of the X-ray source and detector are coordinated with each other; and a controllable inverter circuit connected between the comparison circuit and the control circuit and selectably functioning in a first or in a second operating condition, as the need may be, a correction signal from the comparison circuit being inverted in the first operating condition and being not inverted in the second operating condition.

2. An X-ray system as claimed in claim 1, wherein the comparison circuit functions to convert a first signal generated by one of the signal generators into a comparison signal in to an adjustable weighing code, the correction signal being equal to the difference between the comparison signal and a second signal generated by the second signal generator, whereby the weighing code determines the velocity ratio of the X-ray source and detector.

3. An X-ray system as claimed in claim 1, wherein a velocity selection circuit for controlling the control circuits of the electric motors functions to form from a section-height signal and a movement-width signal a velocity signal which is connected as an input signal for the control circuits of the electric motors, the section-height signal indicating the point of rotation of the connection line between the X-ray source and detector and the movement-width signal indicating an angle to be traversed by the connection line with respect to the point of rotation and a period of time for traversing the angle.

4. An X-ray system as claimed in claim 3, wherein the section-height signal and the movement-width signal have a digital form and are connected to a velocity selection circuit and a weighing code memory, a combination of the section-height signal and the movement-width signal constituting an address for selecting a velocity signal in the velocity selection circuit for controlling the electric motors and for selecting a weighing code in the weighing code memory to urge the instantaneous position of a second electric motor to the instantaneous position of a first electric motor.

5. An X-ray system as claimed in claim 2, wherein the comparison circuit comprises the following components in combination:

counters for counting pulses generated by the signal generators, from which counters a counter position is read periodically;

a first buffer for storing the counter position of a first counter;

selection circuit means which in a first operating condition present the counter position of a second counter directly to a second buffer and in a second operating condition present the said counter position to a weighing code memory;

the weighing code memory in which the weighing code is stored functioning to convert the counter position of the second counter into the comparison signal;

the second buffer being connected for storing either the counter position of the second counter or the counter position which is converted by the weighing code memory;

a subtraction circuit for determining the difference of the contents of the first and second buffers; and a third buffer which stores said difference and which determines the value of the correction signal.

6. An X-ray system as claimed in claim 3, wherein the velocity signal is applied to a rotation control circuit of an electric motor which moves the X-ray source onto the point of rotation of the connection line.

7. An X-ray system as claimed in claim 6, wherein the velocity signal is supplied to the rotation control circuit via a gate circuit, which gate circuit is switchable to a first operating condition or to a second operating condition, in which the velocity signal is respectively cut off and transmitted to the rotation control.

8. An X-ray system as claimed in claim 1 wherein the X-ray source and detector are each driven by means of two motors for moving the X-ray source and detector in two substantially parallel planes in two directions normal to each other, the X-ray source and detector having a constant velocity ratio, the X-ray system comprising at least two weighing code memories and at least two velocity selection circuits connected so that a movement in a first direction can be determined by means of a combination of a first weighing code memory and a first velocity selection circuit and a movement extending at rights angles to the first direction can be determined by means of the combination of the second weighing code memory and the second velocity selection circuit by presenting a section-height signal to both memories and to both velocity selction circuits; a movement-width signal being dependent on time and consisting of two components the first component of which is presented to the memory and to the velocity selection circuit of the first combination and the second component being presented to the memory and to the velocity selection circuit of the second combination.

9. An X-ray system for making a shadow image of a layer of an object, which X-ray system comprises an X-ray source and an X-ray detector, as well as driving means which are designed to move the X-ray source and the X-ray detector with respect to each other in at least substantially parallel planes and with a constant velocity ratio in which the driving means comprise, in combination:

at least one electric motor driving the X-ray source, at least one electric motor driving the X-ray detector, each electric motor being connected to an electronic control circuit to control the number of revolutions of said motor, an electric coupling existing betwen the electric motors, wherein the electric coupling comprises signal generators which are connected to the electric motor and/or to the X-ray radiator and detector driven by electric motors so as to obtain signals which are a measure of the instantaneous position of the X-ray source and detector, with means for generating an adjustable weighing-code; and at least one comparison circuit means connected to combine a first signal generated by one of the signal generators with the adjustable weighing code to produce a comparison signal and to subtract said comparison signal from a second signal generated by the second signal generator to produce a correction signal for a control circuit of one of said motors whereby the movements of the X-ray source and the detector are coordinated with each other, the velocity ratio between said source and said detector being determined by the adjustment of said weighing code.

* * * * *